(12) United States Patent
Vercellotti et al.

(10) Patent No.: US 8,002,783 B2
(45) Date of Patent: Aug. 23, 2011

(54) SURGICAL DEVICE FOR BONE SURGERY

(75) Inventors: Tomaso Vercellotti, Genoa (IT);
Fernando Bianchetti, Genoa (IT);
Domenico Vercellotti, Sestri Levante (IT)

(73) Assignee: Piezosurgery, Inc., Columbus, OH (US)

( * ) Notice: Subject to any disclaimer, the term of this patent is extended or adjusted under 35 U.S.C. 154(b) by 692 days.

(21) Appl. No.: 11/954,676

(22) Filed: Dec. 12, 2007

(65) Prior Publication Data
US 2009/0024118 A1 Jan. 22, 2009

Related U.S. Application Data

(60) Continuation of application No. 10/716,437, filed on Nov. 20, 2003, now abandoned, which is a division of application No. 09/740,937, filed on Dec. 21, 2000, now Pat. No. 6,695,847.

(30) Foreign Application Priority Data

Dec. 21, 1999 (EP) .................................... 99830784

(51) Int. Cl.
*A61B 17/32* (2006.01)
(52) U.S. Cl. ......................... 606/169; 606/79
(58) Field of Classification Search .................. 433/86;
604/67, 74, 123, 151, 911; 606/167–170, 606/79–85, 86 R, 171–183
See application file for complete search history.

(56) References Cited

U.S. PATENT DOCUMENTS

| 2,984,241 | A | | 5/1961 | Carlson |
| 4,188,952 | A | * | 2/1980 | Loschilov et al. .............. 606/79 |
| 4,248,232 | A | | 2/1981 | Engelbrecht et al. |
| 4,473,075 | A | | 9/1984 | Rexroth |
| 4,702,697 | A | | 10/1987 | Linkow |
| 4,832,683 | A | | 5/1989 | Idemoto et al. |
| 5,026,387 | A | | 6/1991 | Thomas |
| 5,115,813 | A | | 5/1992 | Ylander et al. |
| 5,122,134 | A | | 6/1992 | Borzone et al. |
| 5,123,841 | A | * | 6/1992 | Millner ........................ 433/125 |

(Continued)

FOREIGN PATENT DOCUMENTS
EP 0238667 9/1987
(Continued)

OTHER PUBLICATIONS

Non-Final Office Action, United States Patent & Trademark Office, U.S. Appl. No. 10/716,437, filed Nov. 20, 2003, Nov. 29, 2007.

(Continued)

*Primary Examiner* — Thomas C Barrett
*Assistant Examiner* — Larry E Waggle, Jr.
(74) *Attorney, Agent, or Firm* — Vierra Magen Marcus & DeNiro LLP (57) ABSTRACT

A surgical device (1) for bone surgery including a body (2) able to be gripped by the user and a tip (3) mounted at the head of the body and set in vibration at a modulated ultrasonic frequency to operate on bone tissue, the surgical device (1) being particularly suitable for oral surgical procedures such as bone sampling, excision of cysts, third molar extraction, preparation of alveolar sites, creation of an opening into the maxillary sinus (Caldwell Luc), elevation of the maxillary sinus by the crestal route and orthopedic and neurosurgical procedures such as osteoplasty, ostectomy and osteotomy.

18 Claims, 6 Drawing Sheets

U.S. PATENT DOCUMENTS

| | | | |
|---|---|---|---|
| 5,195,960 A * | 3/1993 | Hossain et al. | 604/34 |
| 5,318,570 A | 6/1994 | Hood et al. | |
| 5,342,380 A | 8/1994 | Hood | |
| 5,643,304 A | 7/1997 | Schechter et al. | |
| 5,752,924 A | 5/1998 | Kaufman et al. | |
| 5,776,092 A * | 7/1998 | Farin et al. | 604/22 |
| 5,843,109 A | 12/1998 | Mehta et al. | |
| 5,922,003 A | 7/1999 | Anctil et al. | |
| 5,935,143 A * | 8/1999 | Hood | 606/169 |
| 5,968,007 A * | 10/1999 | Simon et al. | 604/22 |
| 5,997,298 A | 12/1999 | Nowak | |
| 6,017,354 A * | 1/2000 | Culp et al. | 606/170 |
| 6,117,152 A | 9/2000 | Huitema | |
| 6,149,434 A | 11/2000 | Gault | |
| 6,267,594 B1 | 7/2001 | Hugo | |
| 6,695,847 B2 | 2/2004 | Bianchetti et al. | |
| 6,818,001 B2 | 11/2004 | Wulfman et al. | |
| 2004/0030254 A1 | 2/2004 | Babaev | |

FOREIGN PATENT DOCUMENTS

| | | |
|---|---|---|
| EP | 0456470 | 11/1991 |
| EP | 456470 A1 * | 11/1991 |
| WO | 87/05793 | 10/1987 |

OTHER PUBLICATIONS

Response to Non-Final Office Action, U.S. Appl. No. 11/396,593, filed Apr. 4, 2006, Feb. 2, 2009.

Response to Non-Final Office Action, U.S. Appl. No. 10/716,437, filed Nov. 20, 2003, Apr. 24, 2008.

Final Office Action, United States Patent & Trademark Office, U.S. Appl. No. 10/716,437, filed Nov. 20, 2003, Jul. 22, 2008.

Response to Non-Final Office Action dated Feb. 3, 2010, U.S. Appl. No. 11/396,593, filed Apr. 4, 2006.

Response to Final Office Action dated Jun. 22, 2009, U.S. Appl. No. 11/396,593, filed Apr. 4, 2006.

Final Office Action dated May 10, 2010, United States Patent & Trademark Office, U.S. Appl. No. 11/396,593, filed Apr. 4, 2006.

Final Office Action dated Apr. 22, 2009, United States Patent & Trademark Office, U.S. Appl. No. 11.396,593, filed Apr. 4, 2006.

Non-Final Office Action dated Nov. 9, 2009, United States Patent & Trademark Office, U.S. Appl. No. 11/396,593, filed Apr. 4, 2006.

Amendment Under 37 CFR 1.114 Submitted With RCE dated Aug. 24, 2009, U.S. Appl. No. 11/396,593, filed Apr. 4, 2006.

Non-Final Office Action, United States Patent & Trademark Office, U.S. Appl. No. 11/396,593, filed Apr. 4, 2006, Sep. 25, 2008.

Response to Final Office Action, U.S. Appl. No. 10/716,437, filed Nov. 20, 2003, Sep. 30, 2008.

Notice of Allowance and Fee(s) Due dated Jan. 26, 2011, U.S. Appl. No. 11/396,593, filed Apr. 4, 2006.

Non-Final Office Action dated Oct. 1, 2010, U.S. Appl. No. 12/364,720, filed Feb. 3, 2009.

Response to Office Action filed Mar. 1, 2011, U.S. Appl. No. 12/364,720, filed Feb. 3, 2009.

Final Office Action mailed May 11, 2011, U.S. Appl. No. 12/364,720, filed Feb. 3, 2009.

Response to Final Office Action filed Jul. 5, 2011, U.S. Appl. No. 12/364,720, filed Feb. 3, 2009.

\* cited by examiner

SURGICAL DEVICE FOR BONE SURGERY

CROSS-REFERENCE TO RELATED APPLICATIONS

This application is a continuation of U.S. patent application Ser. No. 10/716,437 filed on Nov. 20, 2003 (now abandoned); which is a divisional of U.S. patent application Ser. No. 09/740,937 filed on Dec. 21, 2000 (now U.S. Pat. No. 6,695,847); which claims priority to European Patent Application Serial No. 99830784.7 filed on Dec. 21, 1999.

FIELD OF THE INVENTION

The present invention refers to a surgical device and method for bone surgery. The device is particularly suitable, for example, for orthopedic surgical procedures such as osteotomy, ostectomy, osteoplasty etc. and for oral surgical procedures such as excision of cysts, third molar extraction, preparation of implant sites, creation of an opening into the maxillary sinus and elevation of the endosteum.

BACKGROUND

Bone surgery operations that involve cutting of the bony tissue (osteotomy) and/or modeling thereof (osteoplasty) have hitherto been performed with manual and/or rotary instruments. Manual instruments consist of scalpels and/or chisels operated by hand or with a mallet. Rotary instruments consist of motor-driven milling cutters or disks.

These methods both have serious limitations if they have to be used in difficult situations such as restricted surgical access, anatomically difficult bone conditions and particularly when it is necessary to operate in the vicinity of soft tissue.

The cutting characteristics of the techniques currently in use are unsatisfactory for the following reasons:
the cutting depth is poorly controlled;
the mechanical force is often excessive, therefore cutting directionality is lost and/or accidental fractures are caused; and
cutting is not selective and can therefore damage the soft tissue (for example the vascular nerve bundles).

SUMMARY

The object of the invention is to eliminate these drawbacks by providing a surgical device for bone surgery that makes it possible to perform surgical procedures with the utmost precision and therefore with less risk.

Another object of the present invention is to provide such a surgical device for bone surgery that is practical and versatile. Another object of the present invention is to provide such a device for bone surgery that is capable of cutting the mineralized bone tissue without causing cuts and lesions in the soft tissue, and particularly in the neurovascular structures.

Another object of the present invention is to provide a surgical method for bone surgery that is most accurate, efficient and with less risk for the patient.

Preferred embodiments of the invention will be apparent from the claims.

The surgical device for bone surgery according to the invention provides a handpiece comprising a tip capable of operating on bone tissue. For this purpose, according to requirements, various tips such as chisels, compressors, osteotomes, periosteal or endosteal elevators etc. can be mounted on the handpiece.

The handpiece comprises a transducer, which can be piezoceramic, for example, and serves to generate sound waves that set the tip in vibration. The tip is made to vibrate at a frequency within the sonic and ultrasonic range so that when it comes into contact with the mineralized bone tissue an extremely fine and precise cut is made in said tissue. Compression, compaction and displacement of said tissue is also possible according to surgical requirements.

The surgical device according to the invention can be equipped with a console which provides for the electrical and hydraulic supply to the handpiece. The console has a keyboard that can be operated by the operator to control the control electronics of the handpiece.

The control electronics allow the handpiece to be operated with sonic and/or ultrasonic vibrations, modulated or not at low frequency or with low frequency bursts. In this manner the user can modulate the ultrasound pulses to be transmitted to the tip of the handpiece according to the requirements of the surgical procedure.

The surgical device for bone surgery according to the invention has various advantages.

With the surgical device for bone surgery according to the invention, the cutting action on the bone tissue is produced by variable modulation ultrasonic vibrations that are activated only on the cutting end of the tip that comes into contact with the mineralized tissue to be cut. Consequently, the bone tissue surface affected by the action is extremely small. This allows the surgeon to draw the ideal type of procedure that he intends to carry out on the bone tissue with extreme precision. Thus, for example, the actual cut made by the tip will differ minimally from the ideal cut planned beforehand by the surgeon.

Another advantage of the surgical device according to the invention is provided by the fact that, since the cut is extremely fine, the trauma suffered by the bone tissue due to the friction of the cutting instrument and the resulting heat loss will be minimal.

Furthermore, when the vibrating tip encounters soft tissue, such as a neurovascular structure, it loses its cutting capacity. In fact the soft tissue absorbs the vibrations of the tip without being resected and the energy caused by the vibrations of the tip is dissipated in the form of a slight heat. This can be further reduced by the surgeon's promptness in withdrawing the instrument as soon as he feels that it does not vibrate any more. The transmission of heat into soft tissue, such as neurovascular structures, therefore causes no irreparable damage, as might be that caused by injury or cutting of such structures.

Consequently, if during an operation the surgeon touches a neurovascular structure with the tip, he has plenty of time to withdraw the tip without the problem of causing irreparable damage. Thus use of the surgical device according to the invention makes it possible to solve more severe clinical cases of bone surgery in which it is necessary to operate in the vicinity of neurovascular structures.

For example, the device according to the invention can be used in oral surgery for the following types of operations:
bone sampling in anatomically difficult areas, whether for access or because they are near the nerve endings or where there is extremely little bone tissue;
excision of cysts and/or of inflammatory or phlogistic tissue of the third branch of the trigeminal nerve;
extraction of impacted third molars in the vicinity of the dental alveolus;
preparation of an implant site in the vicinity of nerve endings;
creation of an opening into the maxillary sinus (Caldwell-Luc) without damaging the sinusal membrane; and elevation of the maxillary sinus by the ethmoidal crest route.

The device according to the invention can also be used in orthopedic and neurological surgery, in operations such as:
osteoplasty;
ostectomy; and
osteotomy in the vicinity of neurovascular structures as is the case, for example, in vertebral surgery.

Further characteristics of the invention will be made clearer by the detailed description that follows, referring to a purely exemplary and therefore non limiting embodiment thereof, illustrated in the appended drawings, in which:

DETAILED DESCRIPTION

Figure 1:
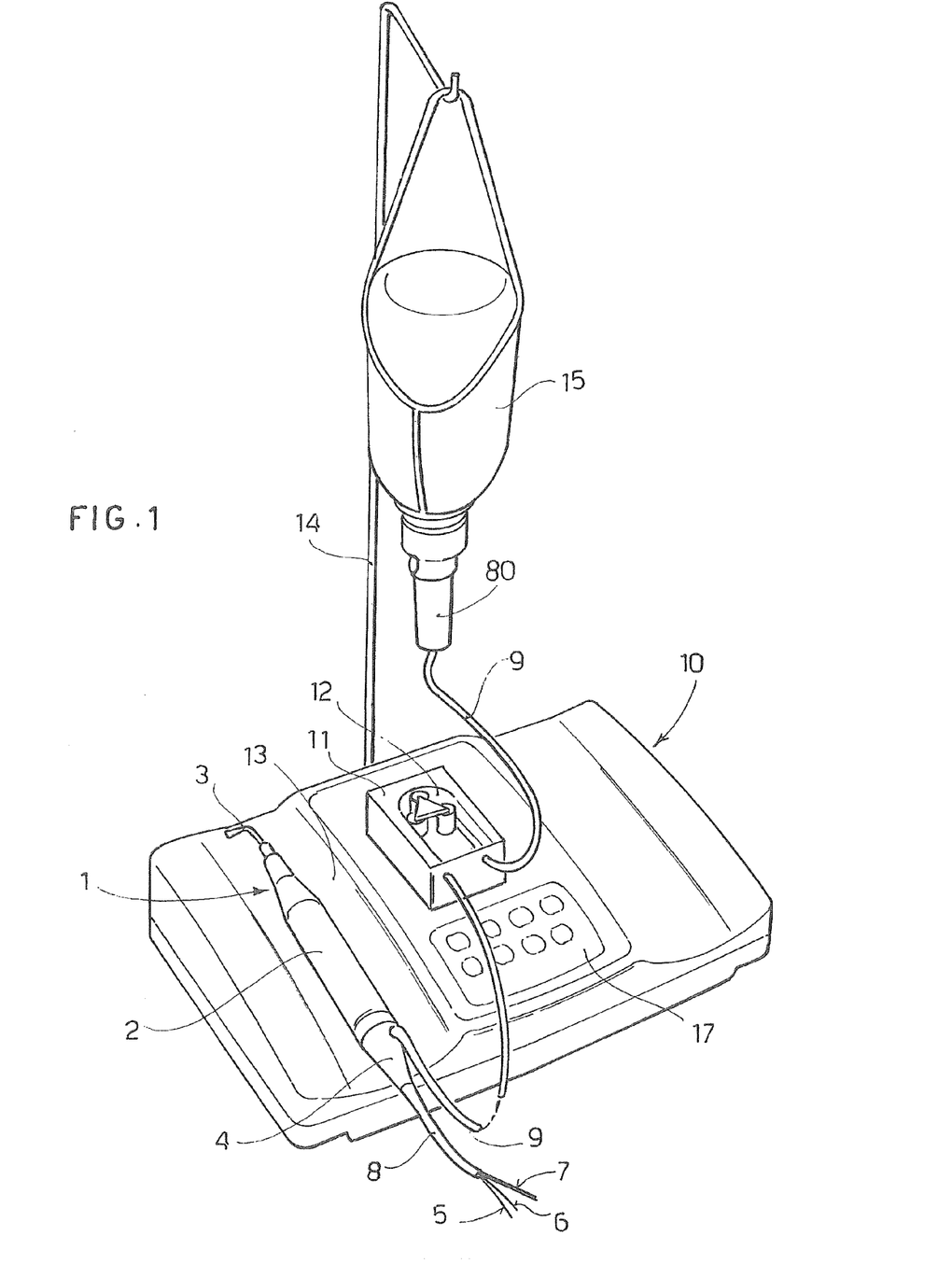
FIG. 1 is an axonometric view of a surgical device for bone surgery according to the invention, complete with equipment for operation thereof.

A surgical device for bone surgery according to the invention, indicated as a whole with reference numeral 1, is described with the aid of the figures. As shown in FIG. 1, the surgical device 1 is a handpiece comprising a body 2, substantially cylindrical in shape so that it can be easily gripped by a surgeon. On the head of the body 2 is mounted a tip 3 having a suitable shape for the various types of bone surgery operations for which the handpiece is intended, as will be described below.

The body 2 of the handpiece is connected to an external connector element 4. The external connector 4 carries two electrical supply cables 5 and 6 and a first hydraulic supply tube 7 which are wrapped inside a sheath 8. The connector 4 also carries a second hydraulic supply tube 9.

The electrical supply cables 5 and 6 are connected to a console 10 that takes its electrical supply from the supply mains or has an independent supply system. The first hydraulic supply tube 7 is connected to a hydraulic supply system, which can be provided in the console 10 or in a separate hydraulic system. The second hydraulic supply tube 9 is connected to a peristaltic pump 11 provided on the console 10.

The peristaltic pump 11 comprises a rotor 12 with a controlled speed of rotation so as to be able to vary the flow rate of the fluid sent, by means of the second tube 9, to the handpiece 1.

The console 10 provides a housing 13 in which the handpiece 1 is positioned and a supporting rod 14 that supports a container 15, which can be a bottle or a bag, for example, which contains a sterile fluid that must be used during the surgical procedure to bathe the surgically treated area. The tube 9 passes inside the peristaltic pump 11 and is inserted in the container 15 through an outlet 80. The sterile fluid from the container 15 is sent through the tube 9 to the peristaltic pump 11 which in turn feeds the sterile fluid toward the handpiece 1. The tube 9 and the outlet 80 of the container 15 can be supplied in sterile disposable packages.

Figure 2:
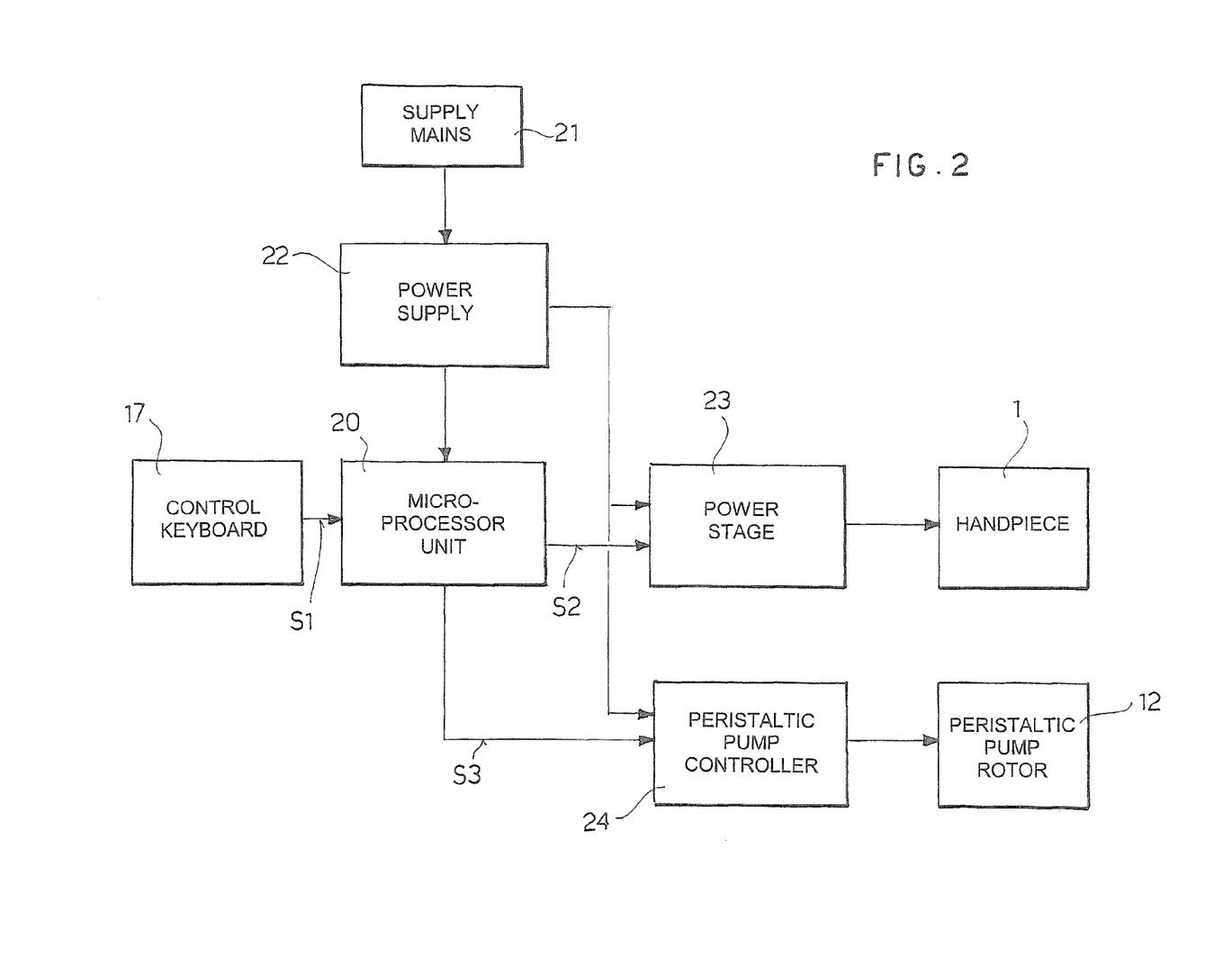
FIG. 2 is a block diagram illustrating operation of the surgical device according to the invention.

On the console 10 a control keyboard 17 that can be operated by the operator to control the microprocessor control unit 10 provided inside the console 10. With reference to FIG. 2, the electrical supply taken from the electrical supply mains 21 is sent to a power supply 22 provided inside the consol 10. The power supply 22 provides electrical power to the microprocessor unit 20, to a power stage 23 and to a control unit 24 of the peristaltic pump 11.

The power stage 23 is able to generate an adequate output current and voltage signal to supply the handpiece 1. The control unit 24 of the peristaltic pump 11 gives out a control signal to operate the rotor 12 of the peristaltic pump 11 so as to feed the sterile fluid from the container 15 toward the handpiece 1.

The keyboard 17 generates control signals S1 toward the input of the microprocessor unit 20. The microprocessor unit 20, on the basis of the control signals S1 received, sends out output control signals S2 and S3 respectively toward the power stage 23 and the control unit 24 of the peristaltic pump 11.

The power stage 23, on the basis of the control signal S2 received, sends the electrical supply to the handpiece 1. The control unit 24 of the peristaltic pump 11, on the basis of the control signal S3 received, regulates the speed of the rotor 12 of the peristaltic pump 11.

Figure 3:
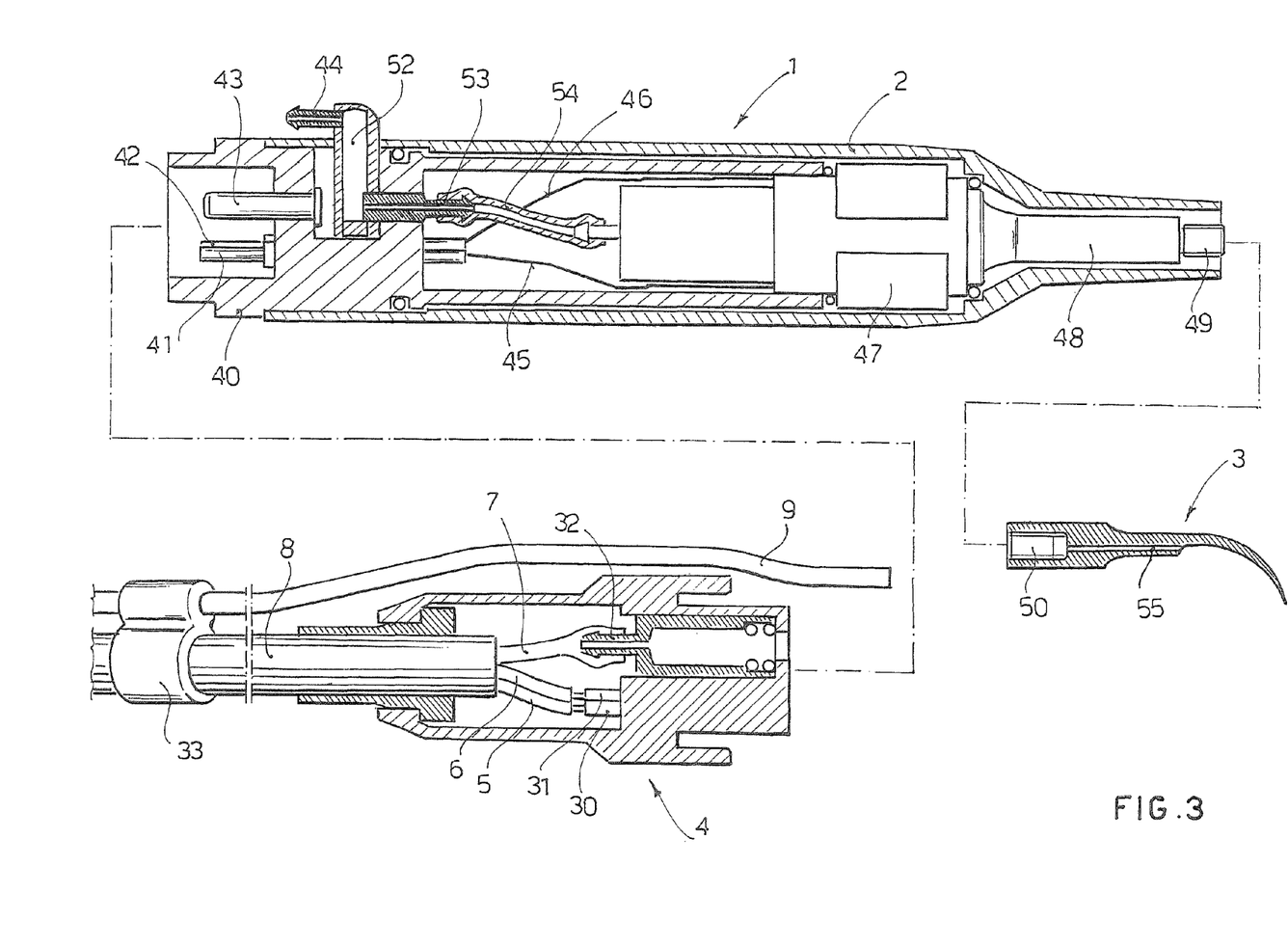
FIG. 3 is an axial section of the surgical device in FIG. 1, with a connector element and a tip exploded.

With reference to FIG. 3, the external connector element 4 provides two electrical contacts 30 and 31 connected to respective wires 5 and 6 of the electrical power supply. Furthermore the connector element 4 provides a hydraulic duct 32 connected to the hydraulic supply tube 7. The tube 9 can be clipped to the sheath 8 by means of a band 33. The external connector element 4 is destined to be inserted into a complementary connecting element 40 provided in the rear part of the handpiece 1.

The connector 40 provides two electrical contacts 41 and 42 destined to come into contact with the contacts 30 and 31 of the connector 4. The connector 40 also provides two ducts 43 and 44 for the hydraulic supply of the handpiece that couple respectively with the duct 32 of the connector 4 and the tube 9. The duct 43 is stopped and serves to confine any fluid coming from duct 32 of the connector. The handpiece is supplied by the fluid through the tube 9 which is inserted into the connector of the duct 44.

The electrical contacts 41 and 42 are connected respectively to electrical wires 45 and 46 which carry the electrical supply to a transducer 47. The transducer 47 is a piezoceramic resonator which must be supplied with alternating voltage and current. The transducer 47 is preferably supplied with a sinusoidal voltage of about 160 V r.m.s. at a frequency ranging between 25 and 30 kHz.

To obtain this type of electrical supply, the console 10 has the power supply 22 and the power stage 23 which act as an electrical transformer, transforming the line voltage from supply mains into a sinusoidal voltage of about 160 r.m.s. at a frequency ranging between 24 kHz and 30 kHz.

The transducer 37, when it is supplied electrically, acts as a sound wave concentrator and sets a tang 48 provided in the head of the handpiece 1 in vibration at an ultrasonic frequency. The tang 48 has a threaded attachment 39 for engagement in a threaded seat 50 of the tip 3. Thus the ultrasonic vibrations are transmitted from the tang 48 to the tip 3.

The microprocessor unit 20 of the console 10, through the control signal S2 controls the power stage 23 so as to allow different operating modes for supplying the transducer 47. In this manner the tip 3 can be set in vibration with ultrasound alone, with ultrasound modulated at low frequency (6-40 Hz), or with a series of low frequency bursts.

This method, which adopts modulation of the vibration of the tip 3, allows the heat that develops on the soft tissue to be minimized because of the dissipation of energy due to the vibration of the tip.

The method that provides for use of modulated ultrasound in low frequency bursts with a variable duty cycle, makes it possible to have a hammering effect of the tip, combined with the ultrasonic vibration efficiency which produces a clean, precise cut in mineralized tissue.

The microprocessor unit 20 is able to perform various functions:
control of the power stage 23;
automatic tuning of the ultrasound that acts on the particular tip 3 used;
setting of the modulation, that is of the duration and frequency of the bursts; and
operation with bursts of increasing or decreasing amplitude.

For these purposes the microprocessor unit 20 has a series of pre-set software programs for use with particular types of tips and in particular clinical setting. These software programs can be updated or other software programs can be stored in the console 10 to make possible applications tested at a later date. Furthermore the user can set operating parameters of his own choice through the control keyboard 17 and store them in the console 10 for subsequent applications.

The hydraulic duct 44 of the connector 40 communicates with a chamber 52 in turn communicating with a duct 53 provided inside the body of the handpiece. The duct 53 is connected to a tube 54 that carries the fluid toward a duct (not shown) inside the tang 48. From the duct inside the tang 48 the fluid spreads into the seat 50 of the tip 3 and through a duct 55 made in the tip 3 it flows toward the outside. In this manner the fluid can irrigate the tissue on which the tip is working, minimizing the operating temperatures due to friction between the tip and the tissue.

In FIGS. 4-9 various types of tips that can be used in the handpiece according to the invention are shown. In these figures the same reference numerals indicate the same or equivalent parts. Each tip provides a seat 50 able to engage with the threaded attachment 49 provided in the handpiece 1. The seat 50 is connected to a stem 60 having an axis substantially parallel to the axis of the handpiece 1. The stem 60 ends in an elbow part 61 connected to the head 62 of the handpiece.

Figure 4:
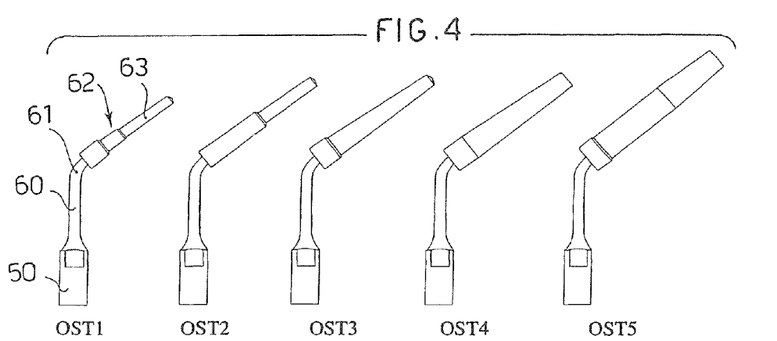
FIG. 4 is a plan view showing five types of osteotomy tips.

FIG. 4 shows five osteotome tips denoted by the abbreviations OST1, OST2, OST3, OST4, and OST5. These tips show a head 62 with a very wide blade 63 used for bone resection. The blade 63 must in fact cause a fracture, breaking the continuity of the skeletal segment without causing removal of bone tissue.

Figure 5A:
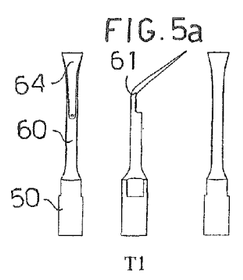
FIGS. 5a, 5b and 5c show respectively three different types of chisel insert and each figure shows a side view, a plan view and a view from the other side.
Figure 5B:
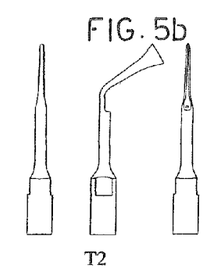
Figure 5C:
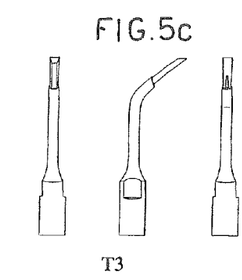

FIGS. 5a-5c show three chisel-type tips denoted by the initials T1, T2 and T3. The chisel tips have a thinner blade 64 that the blade 63 of the osteotomes. In fact the chisel tip is intended for operations in which a very fine, precise cut in the bone tissue is required. For this purpose the blade 64 of the chisel-type tip can have a diamond surface for greater cutting efficiency.

Figure 6:
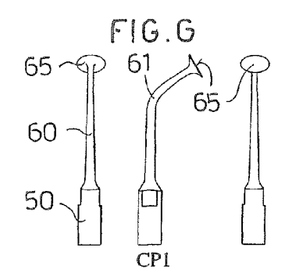
FIG. 6 shows respectively a side view, a plan view and a view from the other side of a compressor tip.

FIG. 6 shows a compressor-type tip is denoted by the initials CP1. This tip has a flattened part 65 in the head to compress the bone tissue.

Figure 7A:
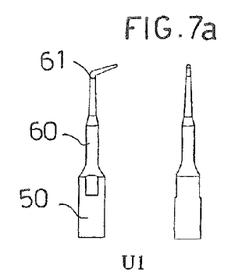
FIGS. 7a and 7b show two different types of universal tip and each figure shows a plan view and a view from the right side, respectively.
Figure 7B:
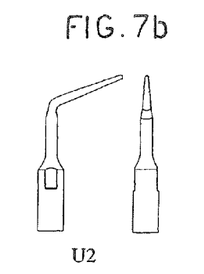

FIGS. 7a and 7b show two universal tips denoted by the initials U1 and U2 which can be used for various types of operation.

Figure 8:
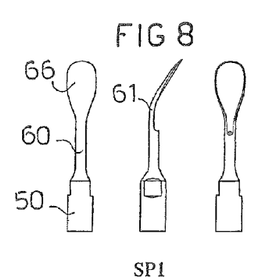
FIG. 8 shows respectively a side view, a plan view and a view from the other side, of a periosteal elevator.

In FIG. 8 SP1 denotes a periosteal elevator tip. This tip has a spoon-shaped head 66 to detach the bone from the membrane (periosteum) surrounding it.

Figure 9A:
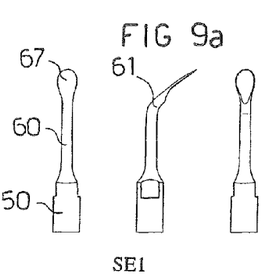
FIGS. 9a and 9b show two different types of endosteal elevator and each figure respectively shows a view from one side, a plan view and a view from the other side.
Figure 9B:
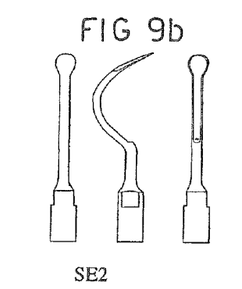

FIGS. 9a and 9b show two endosteal elevators denoted by the initials SE1 and SE2. These tips have a spoon-shaped head 67 smaller in size than the spoon-shaped head 66 of the periosteal elevator. In fact the endosteal elevator must remove the connective tissue (endosteum) that lines the bone cavities.

A surgical technique using the surgical device 1 according to the invention is described with the aid of FIGS. 10a-10f. By way of example a surgical procedure for implantation on an edentulous ridge is described.

Figure 10A:
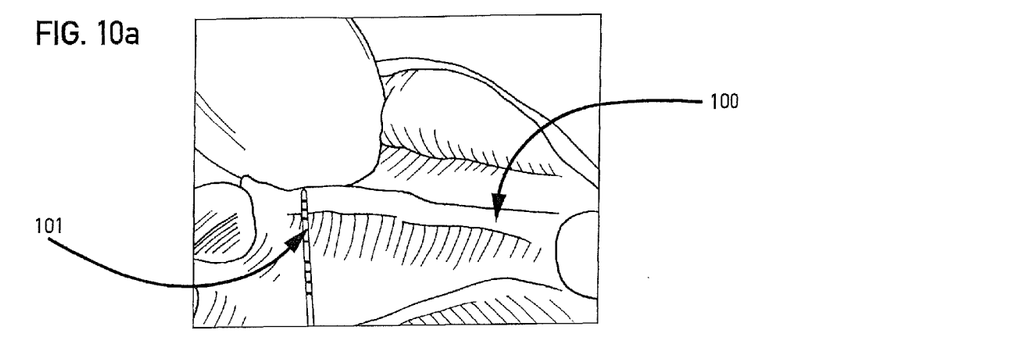
FIGS. 10a-10f show the various stages of a surgical procedure carried out with the surgical device according to the invention.

In FIG. 10a an edentulous ridge 100 is shown at the beginning of the surgical procedure. The thickness of the edentulous ridge 100, measured with a periodontal probe 101, ranges from 2.2 to 2.8 mm. For edentulous ridges with such a small thickness an operation with the instruments of the prior art such as cutters or chisels is impossible or extremely difficult.

Figure 10B:
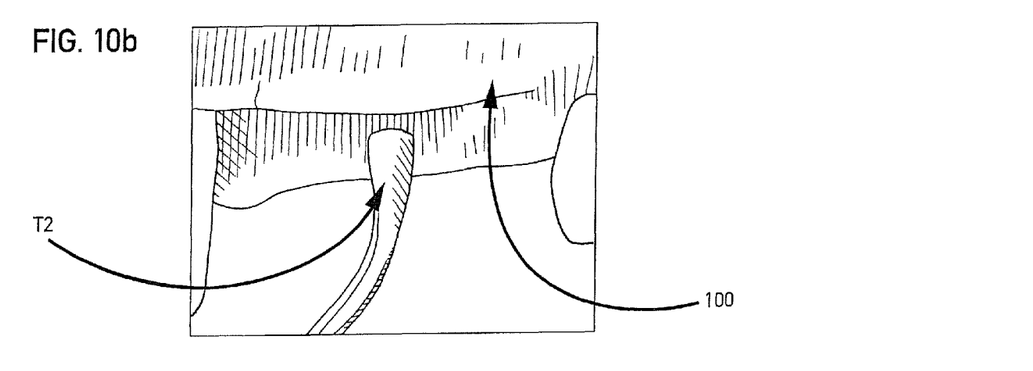

FIG. 10b shows a side view of the edentulous ridge 100 of FIG. 1. This Figure was taken during the surgical operation and shows the type of mucous flap of mixed thickness of the edentulous ridge 100. FIG. 10b shows a type T2 chisel-type tip driven by means of the ultrasound handpiece 1 according to the invention.

Figure 10C:
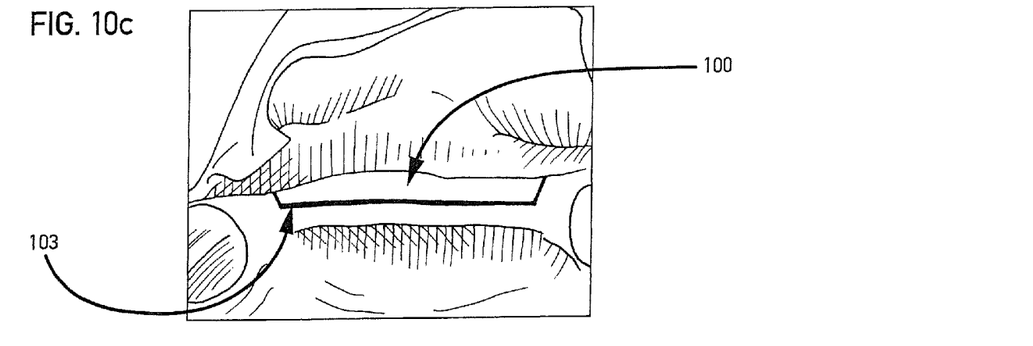

FIG. 10c shows the edentulous ridge 100 after the T2 chisel tip has drawn a horizontal crestal incision 103 with two releasing incisions, one mesial and the other distal. In this figure it can be seen that the cut made by the T2 tip is extremely precise and fine.

Figure 10D:
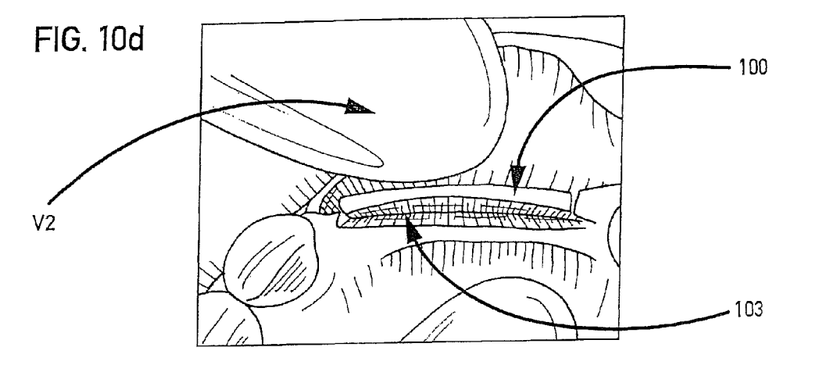

FIG. 10d shows the edentulous ridge 100 after passage of a second type of chisel tip, V2, again mounted on the handpiece 1 according to the invention and operated by ultrasound. The V2 tip has a widened point to separate the vestibular cortical bone wall from the palatal one, according to the bone flap surgical technique.

Figure 10E:
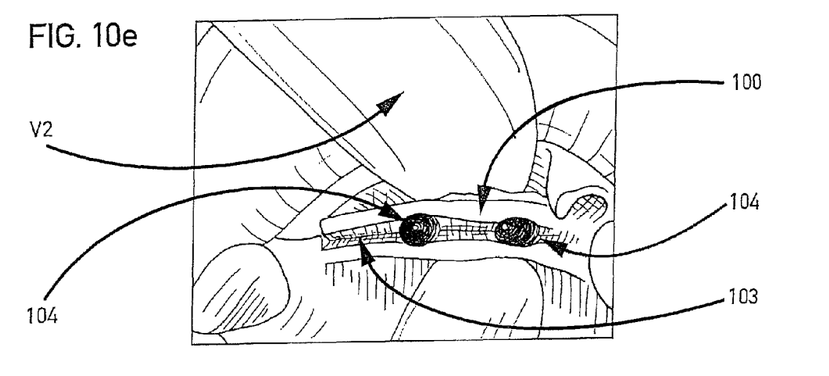

FIG. 10e shows edentulous ridge 100 after two implant sites 104 with a diameter of 2 mm have been created on the bottom of the horizontal crestal incision 103. It has been possible to create implant sites 104 with such a small diameter, using an osteotome tip of the OST1 type described with reference to FIG. 4. The OST1 tip has been mounted on the handpiece 1 and operated by ultrasound.

Figure 10F:
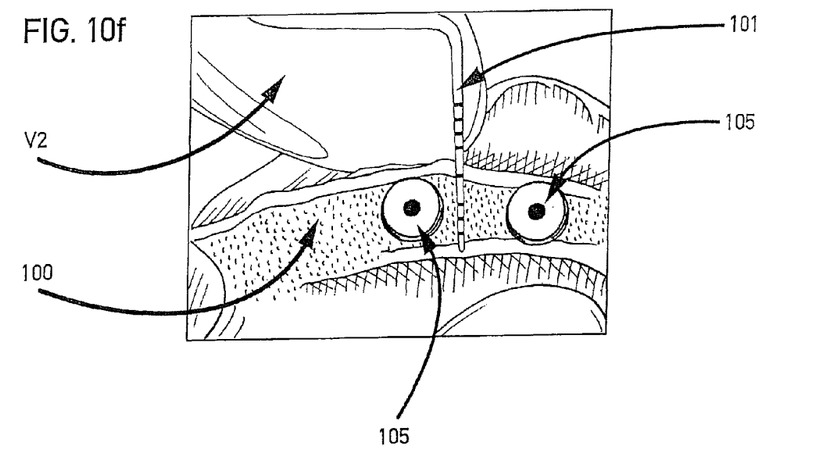

FIG. 10f shows the edentulous ridge 100 three months after the implant. Two implants 105 are visible which have been placed in the respective implant sites 104, in the position for grafting bone material between the cortical walls. The perfectly mineralized bone ridge is visible and, after measurement with the probe 101, it has been possible to detect an increase in the thickness of the bone ridge which has grown from about 2.5 to 5 mm.

The surgical device according to the invention can be used for maxillo-facial and otorhino-laryngol surgical procedures.

The surgical device according to the invention can be used for vertebral laminectomy treatments.

The surgical device according to the invention can be used for hand and foot bone surgery.

What is claimed is:

1. A surgical device comprising:
   a body having a first interface and second interface, the first interface to receive a removable ultrasound tip and the second interface to receive an electrical signal;
   a transducer to provide an ultrasound signal to the first interface in response to the electrical signal; and
   a console including:
      a microprocessor to execute a software program corresponding to the removable ultrasound tip from a plurality of pre-set software programs corresponding to a plurality of different types of removable ultrasound tips, the microprocessor to provide a first control signal in response to execution of the software program and a second control signal; and
      a power stage to provide the electrical signal from a power source in response to the first control signal;
   wherein during a mode of operation, the ultrasound signal has a first amplitude during a first period of time and the ultrasound signal has a second amplitude during a second period of time.

2. The surgical device of claim 1, wherein the surgical device operates in another mode of operation, wherein during the another mode of operation, the ultrasound signal has a constant amplitude and constant frequency.

3. The surgical device of claim 2, wherein the mode of operation is selected in response to the second control signal.

4. The surgical device of claim 3, wherein the console includes a user interface and the second control signal is generated in response to a selection at the user interface.

5. The surgical device of claim 1, wherein the transducer is included in the body, wherein the second interface is adapted to receive fluid from a peristaltic pump included in the console and, wherein the first interface is adapted to output the fluid.

6. The surgical device of claim 1, wherein the removable ultrasound tip is shaped to operate on bone.

7. The surgical device of claim 1, wherein the removable tip is shaped to perform a type of surgery selected from the group consisting of oral, orthopedic and neurological surgery.

8. A surgical device for bone surgery comprising:
   a body having a first and second interface, the first interface to receive a removable ultrasound tip and the second interface to receive an electrical sinusoidal signal and fluid;
   a transducer, included in the body, to provide an ultrasound signal to the first interface in response to the electrical sinusoidal signal; and
   a console including:
      a keyboard to generate a first control signal in response to a user selection;
      a microprocessor to execute a software program corresponding to the removable ultrasound tip from a plurality of pre-set software programs corresponding to a plurality of different types of removable ultrasound tips, the microprocessor to provide a second control signal in response to execution of the software program and the first control signal;
      a power stage to provide the electrical sinusoidal signal from a power source in response to the second control signal;
   wherein the surgical device operates in one of a first and second mode of operation in response to the second control signal,
   during the first mode of operation, the ultrasound signal has a first amplitude and first frequency, and
   during the second mode of operation, an amplitude of the ultrasound signal is modulated at a first low frequency signal.

9. The surgical device of claim 8, wherein the console further includes a pump controller to control the amount of fluid provided to the second interface in response to a third control signal provided by the microprocessor.

10. The surgical device of claim 8, wherein the surgical device operates in one of the first, second and a third mode of operation, during the third mode operation, an amplitude of the ultrasound signal is modulated at a second low frequency signal.

11. The surgical device of claim 10, wherein the surgical device operates in one of the first, second, third and a fourth mode of operation, during the fourth mode operation, an amplitude of the ultrasound signal is modulated at a third low frequency signal and the amplitude is lower than the first amplitude.

12. The surgical device of claim 8, wherein the first low frequency signal has a frequency between approximately 6 Hz and approximately 40 Hz.

13. An ultrasonic surgical device comprising:
   a substantially cylindrical handpiece having a first and second interface, the first interface to receive a removable ultrasound insert shaped to perform surgery and the second interface to receive an electrical sinusoidal signal and fluid;
   a transducer, included in the substantially cylindrical handpiece, to provide an ultrasound signal to the first interface in response to the electrical sinusoidal signal; and
   a console including:
      a keyboard to generate a first control signal in response to a keyboard selection;
      a microprocessor to execute a software program corresponding to the removable ultrasound insert from a plurality of pre-set software programs corresponding to a plurality of different types of removable ultrasound inserts, the microprocessor to provide a second control signal in response to execution of the software program and a first control signal;
      a power stage to provide the electrical sinusoidal signal from a power source in response to the second control signal; and
      a pump controller to control the amount of fluid provided to the second interface in response to a third control signal provided by the microprocessor;
   wherein the surgical device operates in one of a first and second mode of operation in response to the second control signal,
   during the first mode of operation, the ultrasound signal has a first frequency and first amplitude, and
   during the second mode of operation, an amplitude of the ultrasound signal is modulated at a low frequency signal.

14. The surgical device of claim 13, wherein the surgical device operates in one of the first, second and a third mode of operation, during the third mode operation an amplitude of the ultrasound signal is modulated at a second low frequency signal and an amplitude of the ultrasound signal is reduced from the first amplitude.

15. The surgical device of claim 13, wherein the second mode of operation includes the ultrasound signal having a selected predetermined number of cycles per second.

16. The surgical device of claim 13, further comprising a mount to support a container, coupled to a peristaltic pump, to store the fluid, wherein the third control signal is generated to provide a flow rate of the fluid in response to the keyboard selection at the keyboard.

17. The surgical device of claim 13, wherein the removable ultrasound insert is selected from the group consisting of a scalpel, spatula, saw and elevator.

18. The surgical device of claim 13, wherein the low frequency signal has a frequency between approximately 6 Hz and approximately 40 Hz.

* * * * *